(12) United States Patent
Kamps et al.

(10) Patent No.: US 6,884,589 B2
(45) Date of Patent: Apr. 26, 2005

(54) MODEL FOR MYELOID CELL GROWTH, DIFFERENTIATION AND DISEASE

(75) Inventors: Mark P. Kamps, Carlsbad, CA (US); David B. Sykes, La Jolla, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 10/432,057

(22) PCT Filed: Nov. 30, 2001

(86) PCT No.: PCT/US01/45332

§ 371 (c)(1),
(2), (4) Date: May 16, 2003

(87) PCT Pub. No.: WO02/46431

PCT Pub. Date: Jun. 13, 2002

(65) Prior Publication Data

US 2004/0014103 A1 Jan. 22, 2004

Related U.S. Application Data

(60) Provisional application No. 60/250,631, filed on Nov. 30, 2000.

(51) Int. Cl.[7] ................................................. C12Q 1/68
(52) U.S. Cl. ........................... 435/6; 435/325; 530/350; 536/23.4
(58) Field of Search ..................... 435/6, 325; 530/350; 536/23.4

(56) References Cited

U.S. PATENT DOCUMENTS 5,648,248 A    7/1997   Zenke

OTHER PUBLICATIONS

Basharov, J. Cell. Mol. Med., vol. 7, No. 3, 2003, pp. 223–237.*
Hogg, A et al., Inactivation of a c–Myb/estrogen receptor fusion protein in transformed primary cells leads to granulocyte/macrophage differentiation and downregulation of c–kit but not c–myc or cdc2. Oncogene. 1997. 15(24):2885–98.

Kamps, Mark P et al., E2A–Pbx1, the t(1;19) translocation protein of human pre–B cell acute lymphocytic leukemia causes acute myeloid leukemia in mice. Molecular and Cellular Biology. 1993. 13(1):351–7.

Kruse. Ulrich et al., Hormone regulatable neoplastic transformation induced by a Jun–estrogen receptor chimera. Proceedings of the National Academy of Sciences of the United States. 1997. 94:12396–12400.

Mattioni, T et al., Regulation of protien activities by fusion to steroid binding domains, Methods in Cell Biology. 1994. 43 PtA:335–52.

Monks, A et al., The NCI anti–cancer drug screen: A smart screen to identify effectors of novel drug targets. Anti–Cancer Drug Design. 1997. 12(7):533–541.

Picard, D. Regulation of protien function through expression of chlameric proteins. Current Opinion in Biotechnology. 1994. 5(5):511–515.

Sykes, D.B. et al., Cell lines that exhibit conditional myelopoiesis permit the analysis of human leukemic oncoproteins. FASEB Journal. 2000. 14(4)p. A448.

Sykes, D.B. et al., Estrogen–dependent E2a/Pbx1 myeloid cell lines exhibit conditional differentiation that can be arrested by other leukemic oncoproteins. Blood. 2001. 98(8): 2308–2318.

* cited by examiner

Primary Examiner—James Ketter
(74) Attorney, Agent, or Firm—DLA Piper Rudnick Gray Cary US LLP

(57) ABSTRACT

The invention is a genetic construct comprising the coding sequence for a hormone dependent E2a-Pbx1 protein. The invention is the use of the construct to generate hematopoietic cell lines arrested in differentiation upon exposure to the appropriate hormone. Upon removal of the hormone, cells undergo normal, synchronous differentiation providing a system for the study of normal differentiation. Expression of a number of oncogenes in the cells maintains the cells in an undifferentiated state, providing a model for the study the mechanisms of leukemia, and for the testing of pharmacological agents for the treatment and amelioration of the disease.

16 Claims, 1 Drawing Sheet

MODEL FOR MYELOID CELL GROWTH, DIFFERENTIATION AND DISEASE

CROSS-REFERENCES TO RELATED APPLICATIONS

This application claims the benefit of priority of U.S. provisional application Ser. No. 60/250,631 filed Nov. 30, 2000 which is incorporated herein by reference in its entirety.

This invention was made with government support under Grant No. CA56876 awarded by the National Institutes of Health. The United States government has a certain rights in this invention.

BACKGROUND OF THE INVENTION

Molecular pathways of normal hematopoietic cell differentiation, as well as the mechanisms by which oncogenes disrupt this process, remain poorly understood. In normal hematopoietic progenitor cells, a program of specific gene expression orchestrates commitment and differentiation of mature cells to multiple different lineages. In acute leukemias, however, oncoproteins interfere with this genetic program, resulting in the unregulated proliferation of cells that no longer retain the capacity to differentiate normally. In acute myeloid leukemias (AMLs) many known myeloid oncoproteins can block the differentiation of normal progenitors cultured in vitro in the presence of granulocyte-macrophage colony stimulating factor (GM-CSF) or interleukin-3 (IL-3). However, neither the genetic events that underlie normal hematopoietic cell differentiation nor the mechanism through which leukemic oncoproteins interfere with the execution of the program of lineage differentiation are well understood.

A number of genes have been identified that are critically involved in various forms of leukemia. For example, the t(1;19) chromosomal translocation in humans results in the production of E2a-Pbx1, a chimeric oncoprotein containing the transactivation domains of E2a joined to the DNA-binding homeodomain protein Pbx1. E2a-Pbx1 causes T-cell and myeloid leukemia in mice, blocks differentiation in murine myeloid progenitor cells, and transforms fibroblasts. The mechanisms of differentiation arrest are likely accompanied by aberrant expression of tissue specific and developmentally regulated genes. This aberrant tissue specific gene expression is also found in the subset of pre-B cells containing the t(1:19) translocation in humans. The exact mechanism by which E2a-Pbx1 alters gene expression is unclear, but it appears to modulate transcription in cooperation with homeobox gene products. In human pre B-ALL, expression of E2a-Pbx1 correlates with the expression of EB-1, a tyrosine kinase signal transduction gene. Potentially, EB-1 overexpression could interfere with normal signal transduction pathways in proliferation and differentiation.

Primary cells and myeloid cell lines offer useful, but limited, models to approach questions regarding mechanisms of normal myeloid cell growth and differentiation, and how this process goes awry in leukemia. Although primary marrow progenitor cells demonstrate normal granulocytic and monocytic differentiation in IL-3 or GM-CSF, one is limited by the scarcity of cells, the difficulty in isolating homogeneous populations, and the inability to verify expression of non-transforming oncoproteins when using such progenitor cells to study the normal program of myeloid differentiation and the mechanisms by which oncogenes alter this program. Useful myeloid cell lines that demonstrate inducible differentiation in response to changes in cytokines include FDCPmixA4 (GM-CSF+granulocyte colony-stimulating factor [G-CSF]+macrophage colony-stimulating factor [M-CSF]), 32Dlc3 (G-CSF), M1-AML (IL-6), and FDB cells (GM-CSF), whereas those that respond to nonphysiologic stimuli include HL60 (high levels of retinoic acid [RA], 12-o-tetradecanoylphorbal 13-acetate [TPA], dimethyl sulfoxide [DMSO]), EML (GM-CSF and RA), MPRO (RA), NB4 (RA), and U937 cells (RA, TPA, DMSO, or vitamin $D_3$). There are no lymphoid cell lines that demonstrate inducible differentiation. Although these lines supply an unlimited number of clonal cells, most are limited by the fact that they contain undefined genetic changes such that their differentiation is often incomplete, asynchronous, or accompanied by cell death. Because the myeloid cells are already blocked to differentiation in response to either IL-3 or GM-CSF, it is unclear whether induction by other extrinsic factors proceeds through normal differentiation pathways. Furthermore, oncoproteins whose action it is to block differentiation induced by IL-3 or GM-CSF cannot be assayed in these prearrested cell lines.

A murine cell line was derived by Hogg and coworkers using a c-Myb-ER fusion was described. However, clonal c-Myb-ER cell lines were not derived, nor were the cells assayed for their ability to score differentiation arrest by other oncoproteins (Hogg et al. (1997) *Oncogene* 15:2885–98). Thus, the cell line overcomes some of the problems associated with established cell lines; however, the cell line is not clonal. This results in problems with reproducibility and maintenance of expression constructs. It is unclear that such a system would serve as a good model for myelopoiesis or AML.

An optimal hematopoietic cell line model would (1) lack constitutive expression of interfering oncoproteins, (2) exhibit conditional and terminal differentiation in response to biologically relevant molecules such as interleukins and growth factors, and (3) be blocked in an undifferentiated state by common leukemic oncoproteins. None of the cell lines listed above meet all of these criteria.

SUMMARY OF THE INVENTION

The invention is a chimeric cDNA molecule encoding a conditional E2a-Pbx1 protein which contains a hormone binding domain (HBD) from a hormone receptor including, but not limited to, estrogen receptor (ER), glucocorticoid receptor (GR), thyroid hormone receptor (THR), mineralo-corticoid receptor (MR), androgen receptor (AR), and progesterone receptor (PR). The invention is also the protein expressed from the cDNA of the invention. When expressed in the cell in the absence of hormone, it is thought that the chimeric protein is masked by heat shock proteins (HSPs) and is prevented from binding to the cellular DNA. Upon binding of the hormone to its HBD, the chimeric protein is released from the HSP and is free to bind to the cellular DNA activating transcription.

The invention is a primary hematopoietic cell line expressing the cDNA of the invention. The fate of the cell line is dependent upon the source of the cells and the interleukins and growth factors to which they are exposed. For example, bone marrow, fetal liver and embryonic stem cells can be induced to become myeloid cells in the presence of GM-CSF or IL-3. In the presence of IL-7, the same cells will be induced to become lymphocytes. Expression of the construct of the invention in these cells in the presence of hormone results in a differentiation block in the cells. Upon removal of hormone, the cells undergo normal, terminal, synchronous differentiation. However, upon expression of a heterologous leukemic oncoprotein, the cells remain blocked in their undifferentiated state, paralleling the situation seen in leukemia.

The invention is the use of the cell lines to examine the biochemical and genetic pathways that accompany normal differentiation in hematopoietic cells, as well as a system in which to dissect how other leukemic oncoproteins interfere with these pathways. Presently there is no conditional model of differentiation arrest that recapitulates the process seen in leukemia in vivo. Terminally differentiated cells do not divide; therefore, the maintenance of cells in an undifferentiated state is required for the uncontrolled cell division associated with cancer. The cell lines of the system allow for detailed analysis of the mechanisms of the inhibition of differentiation associated with leukemia as established by E2a-Pbx1 or other single oncoprotein.

The invention provides a system for the development and testing of pharmacological agents to develop methods to ameliorate and cure leukemias. By understanding the mechanisms of leukemogenesis, one can design agents to disrupt the mechanisms. In an assay to test for chemotherapeutic activity, the cell lines of the invention are grown in the presence of the appropriate hormone to maintain the cells in a proliferative state. Alternatively, the cells of the invention expressing the conditional E2a-Pbx1 are subjected to another factor (e.g. introduction of a leukemic oncoprotein) that prevents the normal differentiation of the cells in the absence of hormone. Cells are subsequently treated with any of a variety of factors including, but not limited to compounds from combinatorial libraries, developed by rational drug design, or purified from natural products, or genetic constructs in appropriate delivery vectors. In this manner, one can analyze the cells to identify factors that are capable of inducing the cells to differentiate, thereby arresting their unregulated cell division.

The invention is a system for the study of other oncogenes involved in the process of hematopoiesis. The transformed primary cell lines of the instant invention are defined and contain only the conditionally activated E2a-Pbx1-HBD, rather than unknown changes that may exist in cell lines. Thus the effect of the introduction of the oncogene of interest can be determined without interference from other unknown oncogenes or cellular changes. The cooperative effects of oncogenes such as Bcl-2, Ras and Bcr/Abl with E2a-Pbx1 in the process of differentiation and leukogenesis can also be analyzed. The cell lines can also be used to assess the oncogenic potential of various factors including nucleic acids, proteins, growth factors and other bioactive compounds by their ability to maintain differentiation arrest after the withdrawal of hormone.

The invention is a system that allows for the identification of E2a-Pbx1 target genes that mediate the differentiation block as the block can be turned on and off by the addition or removal of hormone. Cells expressing either form of the E2a-Pbx1-HBD constructs can be compared to cells before and after withdrawal of the appropriate hormone, or with cells expressing any of a number of oncoproteins in conjunction with E2a-Pbx1-HBD. Analysis may be performed by any of a number of methods well known to those skilled in the art.

The invention is a system to identify differences between cell fates by providing cell lines that are arrested in cellular differentiation, but not lineage definition. The cells can be released from a differentiation block in a synchronous manner such that a sufficiently large homogenous population of cells can be obtained for study. Analysis of a variety of factors, including but not limited to transcription factors, cell surface markers, protein activation through phosphorylation or other mechanisms, translocation of proteins within the cell, activation of promoter, enhancer and repressor elements, and RNA transcription can be performed by a variety of methods well known to those skilled in the art.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which.

DETAILED DESCRIPTION AND PREFERRED EMBODIMENTS

Figure 1:
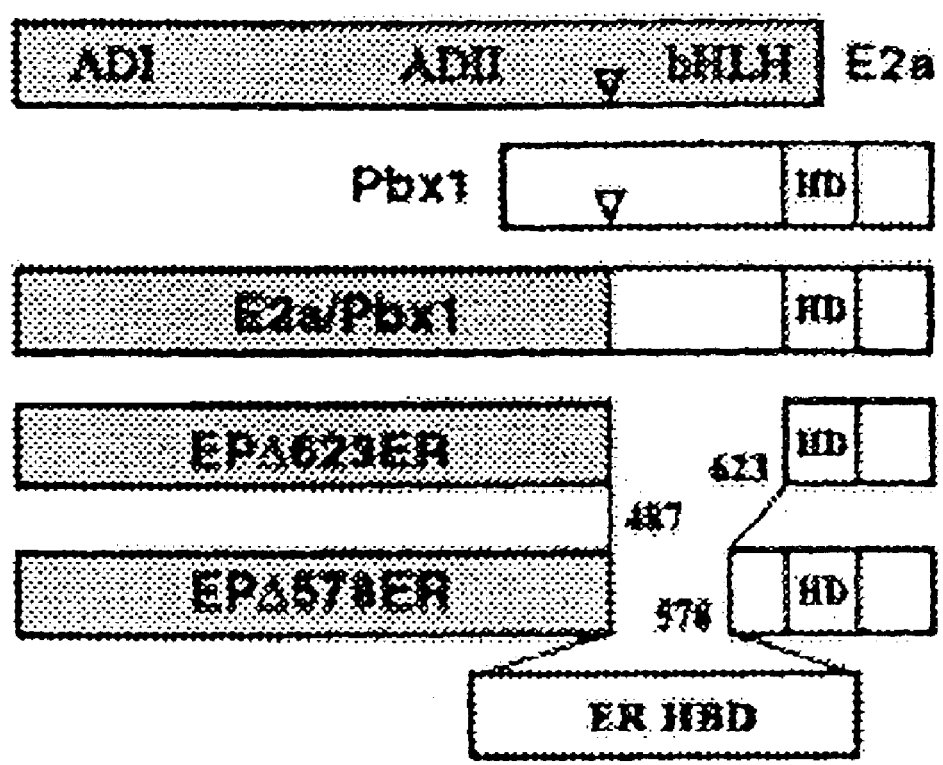
FIG. 1. Estrogen dependent forms of human E2a-Pbx1 are produced by replacement of Pbx sequences with the ER HBD. EP Δ578ER and EP Δ623ER were created by an internal fusion of the HBD (aa 282–595) of the Gly400Val mutant human ER. The HBD replaces the Pbx1 sequences, upstream of the DNA-binding homeodomain, that are dispensable for the biochemical and transforming properties of E2a-Pbx1.

The molecular mechanisms of hematopoietic cell growth and differentiation are not well understood. In normal progenitor cells, differentiation is directed by exposure to growth factors and interleukins directing cells to a specific, terminal and quiescent fate. In acute leukemia, progenitor cells fail to respond normally to differentiation inducing signals and divide uncontrollably. The invention is a cDNA that encodes a protein that acts as a molecular switch to induce a block in differentiation by activation of an E2a-Pbx1 protein. The protein contains a hormone binding domain that allows for the activation of the protein in the presence of hormone. Upon removal of the hormone, the progenitor cells undergo a normal, terminal and synchronous process of differentiation. Thus the cells provide an ideal model for the process of hematopoiesis. However, upon expression of a leukemic oncoprotein in the E2a-Pbx1-ER cells, followed by removal of hormone, the differentiation block is maintained, providing an ideal model for leukemia.

A model of myeloid cell differentiation was established using mouse primary bone marrow cells differentiated in the presence of GM-CSF and an E2a-Pbx1 protein containing the HBD from the estrogen receptor (E2a-Pbx1-ER). Clonal cell lines expressing E2a-Pbx1-ER were blocked in an undifferentiated state in the presence of estrogen, but differentiated normally into granulocytes and monocytes upon removal of estrogen. However, upon expression of any of a number of oncoproteins in the cell, including AML1/ETO, PML/RAR α, Hoxa9, Hoxb8and wild type E2a-Pbx1, the differentiation block was maintained as in AML.

The myeloid clonal cell line expressing E2a-Pbx1-ER described in detail below is an example of the cell lines that can be derived using the method of the invention. The selection of the source of the primary cells is a matter of choice and not a limiting aspect of the invention. Bone marrow, fetal liver and embryonic stem cells from a number of mammalian sources can all be induced to adopt a myeloid fate upon exposure to GM-CSF and IL-3. The same cells can be induced to lymphoid differentiation by exposure to IL-7. Similarly, the HBD selected is a matter of choice. The selection of the HBD is dependent on the effect that the ligand will have on the cell line, preferably none, and the availability of reagents. Such selections are routinely made by those skilled in the art (Mattioni et al. (1994) *Meth in Cell Bio*. 43:335–352, incorporated herein by reference). The appropriate hormone is defined as the hormone that binds the receptor in vivo, e.g. progesterone for the progesterone receptor and glucocorticoid for the glucocorticoid receptor. The appropriate hormone is also defined as any analog, agonist, antagonist or other compound that binds to the hormone binding domain in a specific manner to activate the conditional E2a-Pbx1 fusion protein.

The detailed analysis below describes the use of murine myeloid precursor cells infected with a retrovirus containing the coding sequence of human E2a-Pbx1 fused to the HBD of the human ER. The proteins and genetic elements tested in the system are also derived from both mouse and human demonstrating that there is efficient cross-species interaction. This is not surprising as it is well known that many proteins are well conserved throughout evolution, and that human proteins have been shown to function in species as disparate as mouse and even yeast. Thus, it possible to assay proteins and genetic elements across species in the cell lines of the instant invention.

The invention is not limited by the selection of the use of a specific HBD such as that from the ER in the specific example. Moreover it is not limited by the selection of a compound to bind the ER-HBD. Any estrogen, estrogen analog (e.g. β-estradiol, 4-hydroxytamoxifen) or agonist can be used to activate the E2a-Pbx1-ER fusion protein. For simplicity, the term estrogen is used throughout the application. It should be understood to mean any compound capable of activating the fusion protein in a specific manner.

E2a-Pbx1 is the result of a t(1:19) trauslocation that joins the transactivation domains of E2a with the DNA-binding homeodomain ofPbxl. A conditional E2a-Pbx1 (E2a-Pbx1-ER) was constructed by insertion of the ligand binding domain of the estrogen receptor between the E2a and the Pbx1 domains (FIG. 1), creating a protein that is constitutively expressed, but functionally inactive in the absence of estrogen, estrogen analogs (e.g. estradiol) or other agonist or antagonist. Fusion of the ER HBD to the N- or C- terminus of the full-length E2a-Pbx 1 produced proteins that were estrogen-dependent at the level of transcription, but were unstable (expressed only 10–30% of wild-type) and failed to exhibit estrogen-dependent transformation. Therefore, Pbx1 sequences N-terminal to the homeodomain, which are dispensable for the biochemical and transforming properties of E2a-Pbx1, were replaced with the ER HBD (as detailed in Example 1), creating EP Δ578ER and EP Δ623ER proteins (FIG. 1). Any amount of the Pbx1 domain of the E2a-Pbx1 protein may be deleted between amino acids 487 and 623 and replaced with the RBD of choice. It is not necessary to delete any of the Pbx1 sequence. EP Δ578ER and EP Δ623ER are stable, constitutively expressed, and demonstrate estrogen-dependent biochemical and oncogenic functions.

E2a-Pbx1-ER demonstrated estrogen-dependent activation on artificial luciferase reporter constructs in cells that endogenously contain high and low levels of Hox proteins, namely NIH 3T3 cells and Nalm-6-pre-B cells, respectively. Hox-dependent cooperative transactivation was additionally assayed by co-transfection of E2a-Pbx1with either Hoxc8 or Hoxa9 constructs into Nalm-6 cells with the luciferase reporter construct. Collectively, the strikingly similar patterns of transactivation of luciferase expression in these experiments demonstrated that the activation by wild-type E2a-Pbx1 is unaffected by estrogen, and that EP Δ578ER and EP Δ623ER participate in both Hox-dependent and Hox-independent transcriptional activation in a strictly estrogen dependent manner. The weaker transactivation of luciferase expression of EP Δ578ER, as compared to EP Δ623ER, parallels the weaker cooperativity of the parental EP Δ578 protein with Hox partners in both DNA-binding and transactivation assays. Estrogen (β-estradiol at 1 μM) was sufficient for inducing maximal transactivation, and estrogen induced luciferase activity could be detected within 45 minutes of the addition of estrogen, with maximal activity attained at 8 hours.

The E2a-Pbx1-ER constructs were able to induce conditional and reversible proliferation of fibroblasts in a manner similar to wild-type E2a-Pbx1. NIH 3T3 cell lines stably expressing wild-type E2a-Pbx1, EP Δ578ER and EP Δ623ER were established. In density dependent proliferation assays (see Example 2), wild-type E2a-Pbx1 induced an approximately 3.5 fold increase in total cell number as compared to cells carrying vector alone. In the absence of estrogen, neither EP Δ578ER nor EP Δ623ER stimulated cell proliferation in the absence of estrogen, whereas the addition of estrogen induced a 1.2-fold and 4.5-fold increase in cell number, respectively. This is consistent with the relative transforming strength of EP Δ578ER and EP Δ623ER proteins. Upon removal of estrogen, cells conditionally transformed by EP Δ578ER or EP Δ623ER reverted to the growth densities exhibited by the parental NIH 3T3 fibroblasts, demonstrating that the transformation induced by EP Δ578ER and EP Δ623ER if fully reversible.

Estrogen-dependent immortalization of primary murine marrow GM-CSF-dependent myeloid progenitor cells was observed upon infection with EP Δ578ER and EP Δ623ER. Both EP Δ578ER (12 of 12 cultures) and EP Δ623ER (6 of 6 cultures) immortalized progenitor cells as efficiently as E2a-Pbx1, but only in the presence of 1 μM estrogen. Wild-type E2a-Pbx1-, EP Δ578ER-, and EP Δ623ER-immortalized progenitor cells were phenotypically identical. All cell lines were dependent on GM-CSF, which could be substituted with IL-3. The cells were unresponsive to granulocyte (G)-CSF, or to macrophage (M)-CSF, undergoing apoptotic cell death within 24 hours when cultured in these or in the absence of cytokines.

Removal of estrogen from polyclonal populations of Δ578ER- or EP Δ623ER-immortalized myeloblasts evoked synchronous morphologic differentiation to mature neutrophils (about 80%) characterized by segmented nuclei and lightly staining cytoplasm, and to mature macrophages (about 20%) characterized by their larger size and oval nuclei. Granulocytes were fully differentiated within 5 to 6 days and survived for an additional 24 to 48 hours, whereas monocytes were adherent and stopped proliferating after 7 to 9 days.

The expression of cell surface markers on one population of EP Δ578ER-immortalized cells was characterized by flow cytometry. In the presence of estrogen, cells did not stain with GR-1 (lipopolysaccharide receptor Ly6G) or F4/80 and stained weakly with Mac-1 (CD11b). The removal of estrogen resulted in the dramatic up-regulation of these myeloid differentiation markers, paralleling the morphologic differentiation to granulocytes and monocytes. Functional NADPH oxidase activity, indicative of myeloid differentiation, as evidenced by dark blue deposits following the NBT reduction assay, was observed in fewer than 1% of the progenitor cells in the presence of estrogen, and in more than 99% of the cells cultured 7 days in the absence of estrogen.

Expression of cell surface markers was accompanied by transcriptional activation of a number of differentiation markers. This is not observed in all models of myeloid differentiation. In some systems, phenotypic changes are not accompanied by normal expression of terminal differentiation markers, making the systems inadequate for the study of the process of differentiation. Northern blot analysis was performed on a 9-day time course of RNA samples collected from EP Δ578ER-immortalized cells differentiated in the absence of estrogen. The expression of genes encoding the master transcriptional regulators, primary and secondary granule proteins, components of the NADPH oxidase complex and other markers of myeloid differentiation was examined.

In both the presence and the absence estrogen, progenitor cells demonstrated stable expression of the Ets-family member PU.1, as well as members of the CCAAT/enhancer binding protein (c/EPB α, β, and ε) family of transcription factors, all of which have been shown to be essential for normal myeloid development. C-Myb and c-Myc showed characteristic downregulation late in differentiation, whereas AML1 showed marked (about 5-fold) up-regulation following the removal of estrogen.

The sequential expression of primary and secondary granule genes also accompanied differentiation. Primary granule genes neutrophil elastase and (NE) and myeloperoxidase (MPO) were rapidly upregulated following estrogen withdrawal. This rapid upregulation is important in the context of elucidating differentiation arrest by E2a-Pbx1 by providing a means to identify transcriptional activators within the NE and MPO promoters, of transcriptional activators that are not produced, or transcriptional repressors that are not eliminated in the presence of active E2a-Pbx1. Such genetic defects provide molecular handles to identify the direct E2a-Pbx1 target genes that mediate differentiation arrest.

Secondary granule genes lactoferrin (LF) and neutrophil gelatinase (NG) were not expressed in myeloblasts and were activated at day 2 and day 7 of differentiation, respectively. Examination of the two subunits of the NADPH oxidase complex revealed that $p47^{PHOX}$ was constitutively expressed, whereas $gp91^{PHOX}$ was not expressed until day 4 of differentiation. The regulated expression of $gp91^{PHOX}$ is consistent with the timing of robust NADPH oxidase activity as determined by NBT reduction. The cells also demonstrated transcriptional upregulation of genes encoding cell surface receptors Ly6G (GR-1), CD14 and the G-CSF receptor. Ly6G expression paralleled that seen by flow cytometric analysis and the low level of G-CSF-R expression in progenitor cells is consistent with their G-CSF unresponsiveness.

Conditional immortalization by EP Δ578ER and EP Δ623ER allowed for the examination of whether all progenitors seemingly identical by morphological criteria, were committed to identical patterns of differentiation. Populations of progenitor cells were cloned, clonality was confirmed by retroviral integration analysis using Southern blotting, and phenotypes were examined using light microscopy and Wright-Giemsa staining 5 days after removal of estrogen. Three types of clones exhibiting E2a-Pbx1-mediated conditional myeloid differentiation were identified: bipotential clones that differentiated into both granulocytes and monocytes (ECoM-GM), clones exhibiting restricted granulocytic differentiation (ECoM-G), and one clone exhibiting restricted monocytic differentiation (ECoM-M).

Within 4 days, ECoM-G cells differentiated homogeneously to granulocytes, whereas ECoM-M cells required 7 days for quantitative monocytic differentiation. Both ECoM-G and ECoM-M cells acquired functional NADPH oxidase activity and the ECoM-M cells upregulated non-specific esterase (NSE), a characteristic marker of normal macrophage development. The ECoM-G cells showed dramatic increase in GR-1 (Ly6G) and Mac-1 staining 7 days after estrogen withdrawal, whereas the intensity of the F4/80 staining was significantly reduced. In contrast, the ECoM-M cells did not express GR-1, but were positive for and showed increasing staining of both Mac-1 and F4/80 during monocytic differentiation. Both ECoM-G and ECoM-M cells became functionally phagocytic as demonstrated by the ability to engulf FITC-labeled E. coli BioParticles (see Example 4).

Phenotypic changes following the removal of estrogen were accompanied by reduced proliferation and $G_1$-cell cycle arrest as evidenced by DNA content analysis. Although both ECoM-G and ECoM-M progenitor cells in estrogen had a high S-phase fraction ($G_1$ 48%/$G_2$ 8%/S 44% and $G_1$ 35%/$G_2$ 13%/S 52%), the majority of the cells had accumulated in $G_1$ following 7 days of differentiation in the absence of estrogen ($G_1$ 96%/$G_2$ 2%/S 2% and $G_1$ 83%/$G_2$ 11%/S 6%).

The parallel models of granulocyte and monocyte differentiation allow for the examination of lineage specific gene expression. ECoM-G and ECoM-M cells recapitulated well established patterns of myeloid gene expression including the down-regulation of c-Myb and c-Myc, and the upregulation of Egr-1, microsialin, c-Fos, neutrophil collagenase (NC), c-Fms and macrophage scavenger receptor SRA-1. Zinc finger protein and transcriptional repressor Gfi-1 was down-regulated in both ECoM-G and ECoM-M clones, whereas expression of family member growth factor independent (Gfi)-1 was down-regulated in only the ECoM-M clone, similar to a previous report in which its down-regulation accompanied the cell-cycle arrest, and up-regulation of $p21^{WAF/CIP1}$ during IL-6 induced monocytic differentiation of M1-AML cells. Ear-2 was stably expressed throughout the differentiation of both ECoM-G and ECoM-M cells in contrast to a previous report in which it was shown to be down-regulated during the G-CSF-induced granulocytic differentiation in 32Dcl3 cells and hypothesized to bind and inhibit AML1 activity. Similarly, Ets family member Fli-1 has been reported in human T-cell, B-cell and myeloid leukemia lines and was shown to be critical for hematopoiesis based on a study in a Fli-1 deficient mouse. Expression of the aldoketoreductase mAKRa was restricted to the ECoM-G clone and was stable throughout differentiation, in contrast to a previous report that showed decreased expression following the all-trans-RA (atRA)-induced granulocytic differentiation of EML-C1 and MPRO cells. Expression of Ets-2 was restricted to the ECoM-G clone, which was unexpected given previous reports of Ets-2 expression in normal and transformed macrophages.

Overall, the differences in gene expression between ECoM-G and ECoM-M cells demonstrate that E2a-Pbx1 prevents differentiation but not lineage definition, and that these cell lines are useful models to identify differences between granulopoiesis and monopoiesis.

The cell lines of the invention are also a model system in which to study the inhibition of differentiation arrest due to the expression of a heterologous oncoprotein. A variety of oncogenes were tested for their ability to maintain the differentiation arrest in the E2a-Pbx1-ER cell lines upon withdrawal of estrogen (Examples 6–9). Expression of a number of heterologous oncogenes were able to maintain the cells in a state of differentiation arrest. However, the specific markers expressed in the cells varied depending on the cooperative oncogene expressed. Such cells provide an ideal model for the understanding leukemia as any of a number of cooperative mutations are possible in vivo. Determination of the cooperative mutation by the analysis of markers from patient samples can lead to more efficient therapies for the treatment of disease.

The invention also provides a system for the testing of various pharmacological compounds and therapeutic reagents for the treatment of disease. The ability of a therapeutic agent to promote differentiation induced by a variety of single oncoproteins in a defined background could only be studied using the system of the instant invention. Expression of a heterologous oncogenes in a cell line of the invention allows for the direct comparison of the efficacy of a single compound on cells with identical genetic backgrounds other than the single oncogene. Alternatively, a series of compounds can be tested on cells containing a defined genetic alteration to determine if they are capable of inducing differentiation.

EXAMPLE 1

Construction of estrogen-dependent versions of E2a-Pbx1. In human t(1:19) pre-B ALL, both E2a-Pbx1a (825 amino acids (aa)) and E2a-Pbx1b (742 aa) are expressed, differing only in residues C-terminal to the Pbx1 homeodomain. Sequences encoding the HBD of the ER, residues 282 to 595 of the Gly400Val human ER, with flanking MluI restriction sites, were amplified by high-fidelity polymerase chain reaction (PCR). The Gly400Val mutant ER was used because the point mutation renders the receptor insensitive to the low levels of estrogen found in fetal bovine serum (FBS) as well as to the estrogenic effects of compounds such as phenol red. The estrogen-binding domain was inserted into two versions of E2a-Pbx1b (E2a-Pbx1 Δ487–578 and E2a-Pbx1 Δ487–623) that lack Pbx1 sequences N-terminal to the Pbx1 homeodomain (FIG. 1) that have unique MluI sites in place of the deleted residues, resulting in fusions designated EP Δ578ER and EP Δ623ER, respectively. Thus, the HBD replaces Pbx1 sequences upstream of the DNA-binding homeodomain that are dispensable for the biochemical and transforming properties of E2a-Pbx1. EP Δ578ER and EP Δ623ER were subcloned into the murine stem cell virus (MSCV) retroviral vectors MSCVneo and MSCVpac.

EXAMPLE 2

Analysis of density-dependent growth. The NIH 3T3 fibroblasts were infected with helper-free retrovirus encoding wild-type and inducible versions of E2a-Pbx1. Stably expressing cells, as well as cells transduced with empty vector virus, were selected 7 days in 1 mg/ml G418 in the absence of estrogen. Equivalent numbers of cells were plated in triplicate into 60-mm dishes in the presence and absence of 1 μM estradiol. Half media changes were performed every two days and the total number of live, adherent cells was determined after 14 days. Fold density was calculated in comparison to the number of cells transduced with the empty viral vector.

EXAMPLE 3

Retroviral infection of primary murine marrow progenitor cells. Bone marrow mononuclear cells were isolated on a Ficoll-Paque gradient following harvest from the femurs and tibia of female Balb/c mice injected intraperitonally with 5-fluorouracil (150 mg/kg) 5 days prior to harvest. Marrow progenitor cells were purified by negative selection of lineage-positive cells on a magnetic column with a murine progenitor cell antibody cocktail (Stemcell Technologies, Vancouver, BC, Canada). Progenitor cells were prestimulated for 48 hours in Iscoves modified Dulbecco medium (IMDM) containing 15% fetal bovine serum (FBS), 50 ng/ml stem cell factor (SCF), 25 ng/ml IL-3 and 25 ng/ml IL-6.

Helper-free retrovirus was prepared by calcium phosphate transfection of 293T cells with MSCV retroviral constructs and an ecotropic packaging construct. Then, 25,000 marrow progenitor cells were infected with 1 ml retroviral supernatant (approximate titer $2 \times 10^5$ particles/ml) by spinoculation (2500 g, 2 hours, 22° C.) in the presence of Lipofectamine (1:1000, Gibco BRL). Following spinoculation, the cells were cultured in RPMI media containing GM-CSF and 1 μM β-estradiol, an estrogen analog, as described above. Immortalized myeloid progenitor cells were enriched by the passage of non-adherent cells over the course of approximately 3 weeks.

Single cell clones were prepared by limiting dilution. E2a-Pbx1-mediated conditional Myeloid (ECoM)-GM and ECoM-G clones were established from both populations immortalized by EP Δ578ER and EP Δ623ER, whereas the ECoM-M cell line was derived from a population immortalized by EP Δ623ER.

EXAMPLE 4

Phagocytosis assay. Phagocytosis was assayed using fluorescein isothiocyanate (FITC)-labeled heat killed *Escherichia coli* BioParticles (Molecular Probes, Eugene, Oreg.). The $10^7$ BioParticles and $10^6$ cells were incubated for 1 hour at 37° C. with shaking. Following cytocentrifugation onto Superfrost Plus slides (Fisher, Pittsburgh, Pa.), the nuclei were counterstained with bis-Benzimide (Hoechst 33258, Sigma) and the F-actin counterstained with TRITC-phalloidin (Sigma). Images were captured with DeltaVision deconvolutuion microscope system and the data sets were deconvoluted and analyzed using Soft Worx software (both from Applied Precision, Issaquah, Wash.).

EXAMPLE 5

Flow cytometric analysis. The FITC-labeled monoclonal antibodies GR-1 (ly6G) and Mac-1 (CD11b) were purchased from Pharmagen and F4/80 from Serotec. Then, $10^6$ cells were labeled 30 minutes at 4° C. in phosphate-buffered saline (PBS)/1% FBS/0.1% $NaN_3$, washed, and resuspended in the same buffer with 2 μg/ml propidium iodide (PI). Flow cytometry data were acquired with the program CELLQuest on a bench-top flow cytometer. Live cells were gated for analysis by forward and side scatter for lack of PI staining.

EXAMPLE 6

Retroviral infection of ECoM-G cells with heterologous oncoproteins. Helper-free retrovirus was generated for wild-type E2a-Pbx1, Hoxa7, Hoxa9, Nup98/HoxA9, Hoxb8, AML1/ETO, PML/RARα and PLZF/RARα constructs cloned into the multiple cloning site of the MSCVneo and MSCVpac retroviral vectors. ECoM-G cells (250,000) from 3 different clones were transduced by spinoculation (as described above) and selected 5 days in G418 (1 mg/ml) or puromycin (1 μg/ml). The cells were washed and plated in media without estrogen. Only those cells that were capable of continued and indefinite proliferation in the absence of estrogen were expanded to generate RNA for Northern analysis.

EXAMPLE 7

Analysis of differentiation arrest induced by heterologous oncoproteins in E2a-Pbx1-ER expressing cells. The ECoM cells provide a system in which to dissect the mechanisms of action of oncogenes. Heterologous oncoproteins were introduced into ECoM-G clones by retroviral infection. Expression was verified by immunoblot assay and cells were assayed for the ability to re-establish differentiation arrest following estrogen withdrawal. AML1/ETO, PML/RARα, Hoxa9, Hoxb8 and wild type E2a-Pbx1 prevented granulocytic differentiation of specific clones permitting their continued and indefinite proliferation in the presence of GM-CSF. The resultant pattern of gene expression was consistent with differentiation arrest by the new oncoprotein. Hoxa9, for example, permitted up-regulation of NE, gp91$^{PHOX}$, Ly6G and the G-CSF-R to levels similar to those of primary marrow immortalized by the expression of Hox9a alone. Similarly, whereas AML1/ETO permitted up-regulation of gp91$^{PHOX}$ and Ly6G, the expression of NE and G-CSF-R, whose activation requires AML1 remain low. This pattern is consistent with the dominant negative function of AML1/ETO on AML1 responsive promoters. ECoM-G clones arrested in differentiation by PML/RARα or PLZF/RARα showed RA sensitivity not seen in the parental cells, providing mechanistic evidence of the function of the second oncoprotein. Although parental cells were completely unresponsive to treatment with 10 μM atRA for 4 days, both PML/RARα and PLZF/RARα derivatives stopped proliferating and underwent quantitative granulocytic differentiation. The ECOM cell lines can thus be used for the analysis of the biochemical and genetic mechanisms by which oncoproteins prevent stage specific myeloid differentiation.

EXAMPLE 8

Assay for oncogenic activity of known or unknown proteins. The EcoM cells provide a system in which to examine suspected oncoproteins and their effects on granulocytic differentiation. Both Nup98/HoxA9 and Hoxa7 were capable of arresting ECoM-G cell differentiation following estrogen withdrawal. Neither protein was known to function in this capacity. Despite their equivalent levels of expression, Nup98/HoxA9 was significantly less efficient than either Hoxa7 or Hoxa9 in arresting differentiation precipitated by estrogen withdrawal. This suggested that the mechanism of differentiation arrest by Nup98/HoxA9 was fundamentally different from that of Hoxa7 or Hoxa9. The small fraction (<1%) of ECoM-G cells that continued to proliferate expressed a smaller version of the protein by western analysis, indicating that some form of rearrangement had occurred. Nup98/HoxA9, identified as the product of the t(7; 11) translocation in human myeloid leukemia has also been shown to cause transformation in NIH 3T3 fibroblasts and to cause AML in mice. The pattern of gene expression in Nup98/HoxA9-immortalized ECoM-G cells was similar to that in Hoxa9-immortalized cells, but lacking gp91$^{PHOX}$ expression. Such an experiment could be performed to determine the oncogenicity of a protein or polypeptide by inserting a cDNA into the appropriate viral vector, infecting the cells, assaying for expression, and observing the proliferative capacity of the cells in the absence of estrogen.

EXAMPLE 9

Analysis of cooperativity between E2a-Pbx1-ER and activated oncogenes. The ECoM-G and ECoM-M clones were rendered GM-CSF-independent following infection with retrovirus encoding oncogenic H-Ras$^{L61}$ or Bcr/Abl$^{p190}$. Removal of estrogen from these cells permitted differentiation as assessed by Wright-Giemsa staining. Although the parental EcoM-G cells in the presence of GM-CSF underwent strict granulocytic differentiation (98%), ECoM-G-Ras and ECoM-G-Bcr/Abl cells demonstrated a predominant monocytic differentiation (99% and 65% respectively). In contrast, the differentiation of ECoM-M cells was not morphologically affected by expression of Ras or Bcr/Abl, though mature monocytes expressing Ras were no longer adherent. These morphological results were supported by flow cytometric analysis. Differentiation of ECoM-G cells expressing Ras or Bcr/Abl was accompanied increased F4/80 and decreased GR-1 staining, whereas expression of Ras or Bcr/Abl in ECoM-M cells did not significantly alter GR-1, MAC-1 or F4/80 staining.

These data clearly demonstrate the advantage of the instant invention over the use of cells that have been in culture for extended periods of time that contain unknown genetic alterations. It is clear that the oncogene present and activated have a large affect on the state of differentiation of the cells. By controlling the factors expressed in the cell, one is able to dissect the mechanisms of differentiation and leukemogenesis.

EXAMPLE 10

Assay for chemotherapeutic activity of a compound. A panel of heterologous oncoproteins are introduced into ECoM-G clones by retroviral infection and stable daughter lines are established. Expression is verified by immunoblot assay and cells were assayed for the ability to re-establish differentiation arrest following estrogen withdrawal. AML1/ETO, PML/RARα, Hoxa9, Hoxb8and wild type E2a-Pbx1 are all capable of preventing granulocytic differentiation of specific clones permitting their continued and indefinite proliferation in the presence of GM-CSF. Cells expressing each of the different oncogenes is plated into a 96- or 384-well plate. The cells are exposed to a series of compounds derived from any of a number of sources. Cells are observed to determine if they undergo differentiation and assayed for functional (e.g. NADPH oxidase activity) or expression of cell surface markers of differentiation (e.g. upregulation of GR-1). Compounds that cause differentiation are further analyzed.

Although an exemplary embodiment of the invention has been described above by way of example only, it will be understood by those skilled in the field that modifications may be made to the disclosed embodiment without departing from the scope of the invention, which is defined by the appended claims.

We claim:

1. A cDNA sequence encoding a hormone sensitive E2a-Pbx1 protein comprising a nucleotide sequence encoding a chimeric E2a-Pbx1-hormone binding domain (HBD) protein.

2. A cDNA sequence of claim 1, wherein the HBD is inserted downstream of the E2 a coding sequence and upstream of a DNA-binding homeodomain of the Pbx1 coding sequence.

3. The cDNA sequence of claim 1, wherein the HBD is derived from a hormone receptor selected from the group consisting of estrogen receptor (ER), glucocorticoid receptor (GR), thyroid hormone receptor (THR), mineralocorticoid receptor (MR), androgen receptor (AR), and progesterone receptor (PR).

4. The cDNA sequence of claim 1, wherein the coding sequence of the HBD contains a mutation to decrease the sensitivity of the domain to hormone.

5. A protein encoded by the cDNA of claim 1.

6. A cell expressing the cDNA of claim 1.

7. A hormone-dependent E2a-Pbx1 hematopoietic cell line comprising primary mammalian hematopoietic progenitor cells expressing a hormone dependent E2a-Pbx1 protein expressing an E2a-Pbx1 protein fused to a HBD.

8. The hormone-dependent E2a-Pbx1 hematopoietic cell line of claim 7, wherein the HBD is derived from a hormone receptor selected from the group consisting of estrogen receptor (ER), glucocorticoid receptor (GR), thyroid hormone receptor (THR), mineralocorticoid receptor (MR), androgen receptor (AR), and progesterone receptor (PR).

9. The hormone-dependent E2a-Pbx1 hematopoietic cell line of claim 7, wherein the HBD is inserted downstream of the E2 a coding sequence and upstream of a DNA-binding homeodomain of the Pbx1 coding sequence.

10. The hormone-dependent E2a-Pbx1 hematopoietic cell line of claim 7, wherein the coding sequence of the HBD contains a mutation to decrease the sensitivity of the domain to hormone.

11. The hormone-dependent E2a-Pbx1 hematopoietic cell line of claim 7, wherein the cells undergo differentiation upon withdrawal of hormone.

12. A method for screening for chemotherapeutic factors comprising exposing a hormone-dependent E2a-Pbx1 hematopoietic cell line to its appropriate hormone, expressing a heterologous oncogene within the cells, withdrawing hormone from the cells, exposing the cells to the potential chemotherapeutic factor, and determining if the cells undergo differentiation.

13. The method of claim 12, wherein the hormone-dependent E2a-Pbx1 hematopoietic cell line comprises primary mammalian hematopoietic progenitor cells expressing a hormone-dependent E2a-Pbx1 protein expressing an E2a-Pbx1 protein fused to a HBD.

14. The method of claim 12, wherein the HBD is inserted downstream of the E2 a coding sequence and upstream of a DNA-binding homeodomain of the Pbx1 coding sequence.

15. The method of claim 12, wherein the HBD is derived from a hormone receptor selected from the group consisting of estrogen receptor (ER), glucocorticoid receptor (GR), thyroid hormone receptor (THR), mineralocorticoid receptor (MR), androgen receptor (AR), and progesterone receptor (PR).

16. The method of claim 12, wherein the hormone binding domain contains a mutation to decrease the sensitivity of the domain to hormone.

* * * * *